United States Patent [19]

Piórkowska-Galeska et al.

[11] Patent Number: 5,005,985
[45] Date of Patent: Apr. 9, 1991

[54] METHOD OF DETERMINING THERMAL COEFFICIENT OF MATERIALS

[75] Inventors: Ewa Piórkowska-Galeska; Andrzej Galeski, both of Lód, Poland

[73] Assignee: Polska Akademia Nauk Centrum Badan Molekularnych i Makromolekularnych, Lód, Poland

[21] Appl. No.: 348,070

[22] Filed: May 5, 1989

[30] Foreign Application Priority Data

May 20, 1988 [PL] Poland .................. 272596

[51] Int. Cl.$^5$ ........................... G01N 25/18
[52] U.S. Cl. ........................ 374/44; 374/29; 374/43
[58] Field of Search ............. 374/29, 43, 44

[56] References Cited

U.S. PATENT DOCUMENTS

| | | | |
|---|---|---|---|
| 3,263,485 | 8/1966 | Mahmoodi | 374/44 |
| 3,279,239 | 10/1966 | Arends | 374/44 |
| 3,733,887 | 5/1973 | Stanley et al. | 374/44 |
| 3,971,246 | 7/1976 | Sumikama et al. | 374/44 |
| 4,630,938 | 12/1986 | Piorkowska-Pakzewska et al. | 374/44 |
| 4,859,078 | 8/1989 | Bowman et al. | 374/44 |

FOREIGN PATENT DOCUMENTS

| | | | |
|---|---|---|---|
| 2513342 | 10/1976 | Fed. Rep. of Germany | 374/44 |
| 0225875 | 8/1985 | German Democratic Rep. | 374/44 |
| 0249023 | 12/1985 | Japan | 374/32 |
| 0433389 | 6/1974 | U.S.S.R. | 374/44 |
| 0741125 | 6/1980 | U.S.S.R. | 374/43 |
| 0911275 | 3/1982 | U.S.S.R. | 374/44 |
| 1111084 | 8/1984 | U.S.S.R. | 374/44 |
| 1133525 | 1/1985 | U.S.S.R. | 374/44 |
| 1165957 | 7/1985 | U.S.S.R. | 374/44 |
| 1390554 | 4/1988 | U.S.S.R. | 374/44 |

OTHER PUBLICATIONS

Hager, Jr., "Miniature Thin-Heater Thermal Conductivity Apparatus," Proc. 5th Annual ISA Test Measurement Symposium, New York (Oct. 1968).

Primary Examiner—William A. Cuchlinski, Jr.
Assistant Examiner—Diego F. F. Gutierrez
Attorney, Agent, or Firm—Ladas & Parry

[57] ABSTRACT

A method for determination of the thermal conduction coefficient of a material sample comprises measurement of momentary temperature differences between two opposite surfaces of the material sample and measurement of heat supplied by a heater. Said material sample is placed in a system composed of the heater, two identical reference samples having known thermal conduction coefficient and two heat sinks. The material sample and the heater are sandwiched between the two heat sinks. All of them as so arranged are maintained in thermal contacts with each other. The measurements are made during a continuous linear change of the temperature of the two heat sinks. The thermal conduction coefficient of the material sample is determined on the basis of the following equation:

$$\lambda = \frac{P}{2s} \frac{1}{\Delta T} - \frac{\lambda_1}{2} \frac{1}{l_1}$$

5 Claims, 1 Drawing Sheet

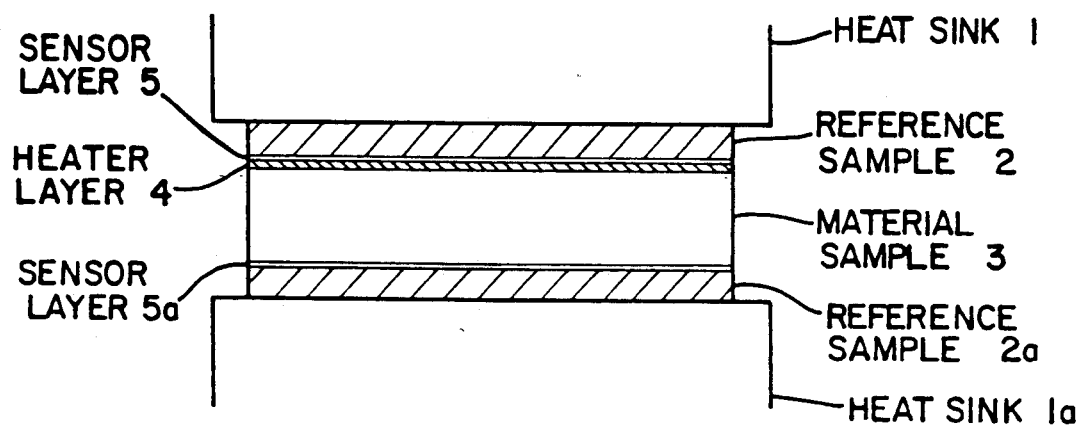

METHOD OF DETERMINING THERMAL COEFFICIENT OF MATERIALS

The subject of the invention is a method of determining thermal conduction coefficient of materials.

Thermal conduction coefficient of materials, $\lambda$, is defined by the equation:

$$\frac{dQ}{ds} = -\lambda \, \text{grad} \, T \tag{1}$$

where: Q is the heat flux in a time unit across a surface s; T is temperature. Spatial changes of the heat flux are described by the equation:

$$\text{div} \frac{dQ}{ds} = -c \frac{\partial T}{\partial t} \tag{2}$$

where: c is the thermal capacity of the material per unit volute; t denotes time.

The combination of equations (1) and (2) gives the thermal conduction equation:

$$\frac{\partial T}{\partial t} = \frac{\lambda}{c} \Delta T \tag{3}$$

Methods of measurement of thermal conduction coefficient of materials comprise indirect and direct ones. Indirect methods rely on determination of thermal conduction coefficient, $\lambda$, or thermal diffusivity a, equal to the ratio of the thermal conductivity, $\lambda$, to the heat capacity, c, per volume unit (a $=\lambda/c$), on the basis of measurement of temperature changes in time at one or several points of a sample. The well known and widely used methods are: the flash method (Parker, Jenkins, Butler, Abbot, J. Appl. Phys. 32, 1679 (1961), Chen Poon, Choy, Polymer, 18, 129 (1977)) and the "hot wire" method (Sandberg, Andersson, Backstrom, J.Phys. E. Sci. Instr. 10, 474 (1977)). In all those methods, the obtained value of thermal conduction coefficient, $\lambda$, is ascribed to certain temperatures close to the average temperature of the sample measurement.

Direct methods of measurement of thermal conduction coefficient comprise measurement of a heat flux across a sample and the temperature difference between opposite surfaces of the sample on the basis of the equation (1). There are many constructions of instruments for measurement of thermal conduction by the stationary method. From the U.S. Pat. No. 3,733,887 an instrument is known, in which a sample is placed between a heat sink and a heat source. The heat sink and source are connected to a temperature control unit. In all cases the known designs are based on the principle of determining thermal conduction coefficient by measurement of the heat flux across a sample of the material at a maintained temperature difference resulting from the imposed heat flux.

Measurements by means of the above-mentioned methods involve a temperature difference between surface of the sample. The temperature difference is usually of the order of a few degrees;

A quasi-stationary method of measurement of thermal conduction coefficient (Eiermann, Hellwege, Knappe, Kolloid Z. 174, 134 (1961)) relies on the measurement of the sum of temperature differences between surfaces of two flat samples, resulting from thermal conduction toward a colder plate placed between the said samples. Assuming that the temperature gradients inside the samples are linear, thermal conduction coefficient, $\lambda$, is calculated from the equation:

$$\lambda = m \, c_w \frac{l}{s} \frac{dT}{dt} (\Delta T_1 + \Delta T_2)^{-1} \tag{5}$$

where: m is the mass of the cold metal plate placed between the samples, $C_W$ is its specific heat; 1 is the thickness of the samples; $\Delta T_1$ and $\Delta T_2$ are temperature differences between surfaces of the samples; dT/dt is the rate of the temperature change of the metal plate. A disadvantage of this method is the assumption of linearity of the temperature distribution inside the samples, which may not be true during a continuous change of the temperature of the heat receiving plate and the samples.

A method of the measurement of thermal conduction coefficient and an instrument for the measurement of thermal conduction coefficient according to the U.S. Pat. No. 4,630,938 (Europ. Pat. No. 0,124,104) enables determination of a continuous dependence of thermal conduction coefficient on the temperature. The known method comprises the determination of momentary differences between temperatrues of both surfaces of the material sample perpendicular to the direction of the heat flux during a continuous temperature change of one of the surfaces of the said sample, preferably linear change in time. The measurement of supplied heat is carried out. The value of thermal conduction coefficient is determined on the basis of the equation:

$$\lambda = \frac{(2Q - b/c) \, l}{2 \, \Delta T} \tag{6}$$

where:
- the thermal conduction coefficient of the material being examined.
- the heat flux across the sample in a unit of time,
- the momentary temperature difference between surfaces of the material sample,
- the thermal capacity of the material being examined per unit volume,
- the thickness of the sample,
- the rate of the temperature change of one surface of the sample.

The instrument for measurement of thermal conduction coefficient according to the U.S. Pat. No. 4,630,938 is provided with a heater, preferably thinner than 1 mm, and equipped with a thin layer temperature sensor. The heater is place between two samples of the material being tested, preferably not thicker than 10 mm. The said samples are in thermal contact with heat sinks which temperature is changed linearly during the time of measurement. A disadvantage of the known method is that in order to calculate thermal conduction coefficient $\lambda$ of the material being tested and its dependence on the temperature, it is necessary to know thermal capacity of the material per unit volume c and its dependence of the temperature. To determine the thermal conduction coefficient, if heat capacity per unit volume c is unknown, one must carry out two measurements at two different preset values of heat fluxes $Q_1$ and $Q_2$ and determine thermal conduction coefficient from the system of two equations (6).

The method according to the invention comprises the determination of momentary differences between temperatures of both surfaces of the material sample in a system composed of two identical reference samples of known thermal conduction coefficient, a heater and a sample of the material. The heater and the sample of the material are placed between said reference samples. Those surfaces of both reference samples, which are in contact with the heater and the material sample, are brought to contact with two heat sinks respectively. The temperatures of the heat sinks are changed preferably linearly in a time. The measurement of the amount of heat supplied by the heater in a time unit is carried out. the value of the thermal conduction coefficient is determined on the basis of the equation:

$$\lambda = \frac{Pl}{2s\,\Delta T} - \frac{\lambda_1 l}{2 l_1} \quad (7)$$

where:
- the amount of heat supplied by the heater in a time unit,
- the thickness of the material sample,
- the surface of the heater,
- the momentary temperature difference between surfaces of the material sample,
- the thermal conduction coefficient of the reference sample,
- the thickness of the reference sample.

When the sample being tested is made of the same material as reference samples, thermal conduction coefficient of reference samples is calculation from the equation:

$$\lambda_1 = \frac{P l l_1}{s\,\Delta T (l + 2 l_1)} \quad (7a)$$

wherein the parameters P, $\lambda$, 1, $l_1$, and $\Delta T$ have the same meansing as those in equation (7).

Since the temperature of the measuring system is copntinuously changed, the thermal conduction coefficient of the sample $\lambda$ is determined on the momentary temperature and on the basis of the equation (7); while the thermal conduction coefficient of reference samples $\lambda_1$ is determined on the momentary temperature and on the basis of the equation (7a).

The measurements may be carried out at various rates of temperature changes of the heat sinks as well as with various levels of heat supplied by the heater. The continuous temperature change of surfaces of both reference samples is preset directly on the surface of said samples or through the intermediary of a good heat conductor.

An instrument according to the invention comprises a material sample placed between two reference samples made of the material of known thermal conduction coefficient. Between the material sample and the first reference sample a thin layer heater and a first temperature sensor are placed. Between the material sample and the second reference sample, a second temperature sensor is placed. Both reference samples are in good thermal contact with two heat sinks respectively. The temperatures of the heat sinks are changed during measurement, preferably linearly with time. Heat sinks consist of a solid body well conducting heat and a stream of gas or liquid, or only the stream of gas or liquid.

The heater may be provided with a heated guard ring. The heater, the first temperature sensor and the heated guard ring are made by the thin-layer technology and assembled into a single element having a thickness smaller than 200 um. The first reference sample may be permanently connection with said element and a first heat sink. The second reference sample may be permanently connected with the second temperature sensor and a second heat sink.

The material sample and both reference samples are of thickness less than 10 mm. Transverse dimensions of the material sample and both reference samples are at least 10 times bigger than the thickness of the samples.

An advantage of the method according to the invention in comparison with the known method is that the thermal conduction coefficient of the material sample and its dependence on the temperature can be determined when heat capacity per unit volume and its dependence on the temperature of said material sample is unknown, by means of only a single measurement with the continuous change of the temperature of the heat sinks.

Moreover, only one sample is used for the measurement. Hence, it is possible to avoid errors resulting from differences between samples. Such errors occur when more than one sample are used simultaneously as in those known methods.

Besides, the method or the instrument according to the invention enables the use of thin samples, which, in turn, allows to conduct the measurement of thermal conductivity at as small as about 1°K differences of temperatures between surfaces of the material sample. Owing to this the momentary temperature of the measurement is well determined.

Moreover, owing to the large transverse dimensions of the samples with respect to their thickness the transverse temperature gradient is minimized. The heated guard ring completely eliminates the transverse temperature gradient. The placement of the material sample and the heater between the reference samples eliminates convection of heat and heat dissipation beyond the heat sinks.

The invention will be explained in more detail hereinbelow.

The method of the continuous measurement of thermal conduction coefficient is based on the continuous measurement of the momentary temperature difference between the opposite surfaces of the material sample to be tested. The measurement is carried out in a symmetrical system, where between two heat sinks, two identical flat reference samples are placed. They are made of the materail of known thermal conduction coefficient. The material sample to be tested and the heater and temperature sensors are placed betwen the reference samples.

The temperature of heat sinks is changed linearly. The temperature in the samples in the function of time and spatial variables and satisfies and differential equations:

$$\nabla^2 T - \frac{C_1}{\lambda_1} \frac{\partial T}{\partial t} = \frac{Q_2\,\partial(x)}{\lambda_1} \quad (8a)$$
for $0 > x > -l_1$ $$\nabla^2 T - \frac{c}{\lambda} \frac{\partial T}{\partial t} = \frac{-Q_1\,\partial(x)}{\lambda} \quad (8b)$$
for $l > x > 0$ $$\nabla^2 T - \frac{C_1}{\lambda_1} \frac{\partial T}{\partial t} = \frac{-Q_1\,\partial(x - l)}{\lambda_1} \quad (8c)$$
for $l + l_1 > x > l$ where: $\delta(x)$ is the Dirac's function, $c_1$ and $\lambda_1$ denote capacity per unit volume and thermal conduction coefficient of the material of reference samples; $c$ and $\lambda$ denote heat capacity per unit volume and thermal conduction coefficient of the material sample to be tested; $l_1$ denotes the thickness of the reference samples; $l$ denotes the thickness of the material sample being tested; x denotes the space coordinate; T denotes temperature; t denotes time; $Q_1$ and $Q_2$ denote heat fluxes flowing into the samples and have the relation of:

$$Q_1 + Q_2 = P/s \tag{9}$$

where: P denotes amount of heat of the heater; s denote the surface of the heater.

Initial conditions brought about by the heat supplied by the heater are as follows:

$$T(x,0) = f(x) \tag{10}$$

where: $f(x)$ is a function independent of time $$T(-l,0) = 0 \tag{11a}$$

$$T(0,0) = T_0 \tag{11b}$$

$$Ti \; T(l,0) = T_1 \tag{11c}$$

$$T(l+l_1,0) = 0 \tag{11d}$$

Boundary conditions are the following:

$$T(-l_1,t) = bt \tag{12a}$$

$$T(l+l_1,t) = bt \tag{12b}$$

where: b denotes the constant rate of the temperature change of the heat sinks.

Equations (8a-c) can be solved by separtion of variables:

$$T(x,t) = u(x,t) + (x,t) \tag{13}$$

Function $u(x, t)$ satisifes differential equations of:

$$\nabla^2 u - \frac{C_1}{\lambda_1} \frac{\partial u}{\partial t} = \frac{Q_2 \, \partial(x)}{\lambda_1} \tag{14a}$$
for $0 > x > -l_1$ $$\nabla^2 u - \frac{C}{\lambda} \frac{\partial u}{\partial t} = \frac{-Q_1 \, \partial(x)}{\lambda} \tag{14b}$$
for $l > x > 0$ $$\nabla^2 u - \frac{C_1}{\lambda_1} \frac{\partial u}{\partial t} = \frac{-Q_1 \, \partial(x-l)}{\lambda_1} \tag{14c}$$
for $l+l_1 > x > l$ with initial and boundary conditions:

$$u(x,0) = f(x) \text{ for } l+l_1 \leq x \leq -l_1 \tag{15a}$$

$$(-l_1,t) = 0 \tag{15b}$$

$$u(l+l_1,t) = 0 \tag{15c}$$

The function $u(x,t)$ can be substituted by a sum of two functions:

$$u(x,t) = u_1(x) + u_2(x,t) \tag{16}$$

The function $u_1(x)$ satisfies the equations:

$$\nabla^2 u_1 = \frac{Q_2 \, \partial(x)}{\lambda_1} \text{ for } 0 > x > -l_1 \tag{17a}$$

$$\nabla^2 u_1 = \frac{-Q_1 \, \partial(x)}{\lambda} \text{ for } l > x > 0 \tag{17b}$$

-continued $$\nabla^2 u_1 = \frac{-Q_1 \, \partial(x-l)}{\lambda_1} \text{ for } l+l_1 > x > l \tag{17c}$$

and boundary conditions:

$$u_1(-l_1) = 0 \tag{18a}$$

$$u_1(0) = T_0 \tag{18b}$$

$$u_1(l) = _1 \tag{18c}$$

$$u_1(l+l_1) = 0 \tag{18d}$$

Solutions of equations (17a-17c) are of the following forms:

$$u_1(x) = \frac{T_0}{l} x + T_0 \text{ for } 0 > x > -l_1 \tag{19a}$$

$$u_1(x) = \frac{T_1 - T_0}{l} x + T_0 \text{ for } l > x > 0 \tag{19b}$$

$$u_1(x) = \frac{T_1}{l_1}(l + l_1 - x) \text{ for } l+l_1 > x > l \tag{19c}$$

The function $u_2(x,t)$ satisfies the equations:

$$\nabla^2 u_2 - \frac{C_1}{\lambda_1} \frac{\partial u_2}{\partial t} = 0 \text{ for } 0 > x > -l_1 \tag{20a}$$

$$\nabla^2 u_2 - \frac{C}{\lambda} \frac{\partial u_2}{\partial t} = 0 \text{ for } l > x > 0 \tag{20b}$$

$$\nabla^2 u_2 - \frac{C_1}{\lambda_1} \frac{\partial u_2}{\partial t} = 0 \text{ for } l+l_1 > x > l \tag{20b}$$

and conditions:

$$u_2(-l_1,t) = 0 \tag{21a}$$

$$u_w(l+l_1,t) = 0 \tag{21b}$$

The function $u_2(x,t)$ is identically equal zero:

$$u_2(x,t) + 0 \text{ for } l+l_1 \leq x \leq 31\;1 \tag{22}$$

The function $w(x,t)$ is the solution of equations:

$$\nabla^2 W - \frac{C_1}{\lambda_1} \frac{\partial w}{\partial t} = 0 \text{ for } 0 > x > -l_1 \tag{23a}$$

$$\nabla^2 W - \frac{c}{\lambda} \frac{\partial w}{\partial t} = 0 \text{ for } l > x > l \tag{23b}$$

$$\nabla^2 W - \frac{C_1}{\lambda_1} \frac{\partial w}{\partial t} = 0 \text{ for } l+l_1 > x > l \tag{23c}$$

with boundary and initial conditions:

$$w(x,0) = 0 \text{ for } l+l_1 \leq x \leq -1 \tag{24a}$$

$$Ti \; w(-l_1,t) = bt \tag{24b}$$

$$w(l+l_1,t)bt \tag{24c}$$

The function $w(x,t)$ can be determined by solving the equations (23a—23c) with conditions (24a-24c) by the Laplace transform method. The function $w(x,t)$ has the form:

$$w(x,t) = b\left[t + \frac{x^2 - l_1^2}{2a_1} - \frac{\lambda l}{2\lambda_1 a}(x + l_1)\right] + \quad (25a)$$

$$\frac{2b}{a} \sum_{m=1}^{\infty} \frac{(1 - \sigma)\cos[\alpha_m(0.5 l + yx)] + (1 + \sigma)\cos[\alpha_m(0.5 l - xy)]}{H \alpha_m^3 \exp(\alpha_m^2 at)}$$

for $-l_1 < x < 0$ $$w(x,t) = b\left[t + \frac{x^2 - xl}{2a} + \frac{l_1^2}{2a_1} - \frac{\lambda l_1 l}{2\lambda_1 a}\right] + \quad (25b)$$

$$\frac{4b}{a} \sum_{m=1}^{\infty} \frac{\cos[\alpha_m(x - 0.5l)]}{H \alpha_m^3 \exp(\alpha_m^2 at)}$$

for $0 < x < l$ $$w(x,t) = b\left[t + \frac{(l - x)^2 - l_1^2}{2a_1} + \frac{\lambda l}{2\lambda_1 a}(x - l - l_1)\right] + \quad (25c)$$

$$\frac{2b}{a} \sum_{m=1}^{\infty} \frac{(1 - \sigma)\cos\{[\alpha_m[0.5 l + y(l - x)]\} + (1 + \sigma)\cos\{\alpha_m[0.5 l + y(x - l)]\}}{H \alpha_m^3 \exp(\alpha_m^2 at)}$$

for $l < x < l + l_1$ where:

$$H = (\sigma + 1)(0.5 l + yl_1)\sin[\alpha_m(0.5 l + yl_1)] + \quad (26)$$

$$(l - \sigma)(0.5 l - yl_1)\sin[\alpha_m(0.5 l - yl_1)]$$

and $\alpha_m, m = 1, 2 \ldots$ are solutions of the equation:

$$(\sigma + l)\cos[\alpha_m(0.5 l + yl_1)] + \quad (27)$$

$$(l - \sigma)\cos[\alpha_m(0.5 l - yl_1)] = 0$$

where: $y = (a/a_1)^{0.5}$, $= \lambda/(Y\lambda_1)$, a and $a_1$ denote thermal diffusivities of the sample being tested and the reference samples determined by dependencies $a = \lambda/c$, $a_1 = \lambda_1/c_1$.

The following dependence results from equations (24a–25c):

$$w(0,t) = w(l,t) = b\left[t + \frac{l_1^2}{2a} - \frac{\lambda l_1 l}{2\lambda_1 a}\right] + \quad (28)$$

$$\frac{4b}{a} \sum_{m=1}^{\infty} \frac{\cos(0.5 \alpha_m l)}{H \alpha_m^3 \exp(\alpha_m^2 at)}$$

The function w(x,t) describes that part of the momentary temperature distribution in the samples, which is only brought about by the linear temperature change of the heat sinks and not by the flow of heat supplied by the heater.

Finally, the momentary temperature distribution in the sample material being tested is described as follows:

$$T(x,t) = \frac{T_1 - T_0}{l} x + T_0 + w(x,t) \quad (29)$$

The momentary temperature difference between surfaces of the material sample being tested is:

$$\Delta T(t) = T(0,t) - T(l,t) = \frac{T_0 - T_1}{l} l + w(0,t) - w(l,t) \quad (30)$$

$$\Delta T(t) = T_0 - T_1 \quad (31)$$

On the basis of the equations (17) and (19) the following dependencies can be derived:

$$\frac{T_0}{l_1} = \frac{Q_2}{\lambda_1} \quad (32a)$$

$$\frac{T_0 - T_1}{l} = \frac{Q_1}{\lambda} \quad (32b)$$

$$\frac{T_1}{l_1} = \frac{Q_1}{\lambda_1} \quad (32c)$$

The following dependence results from equations (28) and (29):

$$\Delta T(t)\left(\frac{2\lambda}{l} + \frac{\lambda_1}{l_1}\right) = \frac{P}{s} \quad (33)$$

The thermal conduction coefficient of the material sample being tested, $\lambda$, can be derived from equation (33):

$$\lambda = \frac{P l}{2 s \Delta T} - \frac{\lambda_1 l}{2 l_1} \quad (34)$$

Neither the heat capacity of the material sample being tested nor the temperature change rate appears in this formula. It is sufficient to carry out measurement of the momentary temperature difference $\Delta T$ during continuous temperature changes within the required temperature range.

When the sample being tested is made of the same material as the reference samples ($\lambda = \lambda_1$), the equation (34) assumes the form:

$$\Delta T(t) \lambda_1 \left(\frac{2}{l} + \frac{l}{l_1}\right) = \frac{P}{s} \quad (35)$$

On the basis of the equation (35), thermal conduction coefficient of the material of the reference samples $\lambda_1$ can be determined:

$$\lambda_1 = \frac{P l l_1}{s \Delta T(l + 2 l_1)} \quad (36)$$

It results from equations (35) and (36) that the dependence thermal conduction coefficient of the material of reference samples on the temperature can be determined by using tested samples made of the same material as the reference samples.

The instrument according to the invention is shown in the drawing as an example of its embodiment. The instrument comprises two heat sinks, which are two metal blocks 1, 1a having dimensions of $25 \times 35 \times 5$ mm and connected to a programmed control unit for changing temperature linearly within a time period. In blocks 1, 1a platinum resistance thermometers are placed and designed to measure the momentary temperature of said blocks. Resistance thermometers function at the same time as sensors for controlling the temperature of blocks 1, 1a by means of heating or cooling the flowing gas. Blocks 1, 1a are in a thermal contact with the first reference sample 2 and the second reference sample 2a of known thermal conduction coefficient. Between the reference samples 2, 2a, a material sample to be tested 3 is placed. Between the first reference sample 2 and the sample 3 of the material to be tested there is a heater 4 placed and equipped with a heated guard ring and a first temperature sensor 5. The heater 4 with the heated guard ring and the first sensor 5 are assembled into a single element made by thin-layer technology and as a whole are less than 200 um thick. Between the second reference sample 2a and the sample of the material to be tested 3, a second thin-layer temperature sensor 5a is placed. The thickness of the heater 4 and temperature sensors 5, 5a is insignificant in comparison with the thickness of all the samples 3, 2, 2a.

The sample of the material being tested 3 is in a thermal contact with the heater 4 and the temperature sensor 5a. The reference sample 2 is in a thermal contact with the heater 4 and the heat sinks 1. The reference sample 2a is in a thermal contact with the temperature sensor 5a and the heat sink 1a. All samples 3, 2, 2a are of equal thickness and preferably less than 10 mm. Transverse dimensions of all samples 3, 2, 2a are 10 times bigger than the thickness of the said samples.

The first reference sample 2 is connected permanently with the heater 4, the first temperature sensor 5 and the first heat sink 1. The second reference sample 2a is connected permanently with the second temperature sensor 5a and the second heat sink 1a.

The tested material sample 3 and the reference samples 2 and 2a can be also made of the same material. In this case, by means of the instrument according to the invention, the thermal conduction coefficient of reference samples 2, 2a is also determined.

We claim:

1. A method for determining thermal conduction coefficient of a material sample having two opposite surfaces, compriisng the steps of:
    placing said material sample in a system composed of a heater, a first and second heat sinks, a first and a second identical reference samples having known thermal conduction coefficients, said first reference sample being in thermal contact with the first heat sink, said second reference sample being in thermal contact with the second heat sink, said material sample and said heater being positioned between the first and the second reference samples and maintaining thermal contacts therewith;
    supplying an amount of heat in a time unit by the heater so as to give rise to a heat flux across the samples;
    measuring sasid amount of supplied heat during a preferably continuously linear change of the temperature of said heat sinks;
    measuring a momentary temperature difference between the two opposite surfaces of the material sample; and
    determining the thermal conduction coefficient of the material sample for the momentary temperature of the system on the basis of the following equation:

$$\lambda = \frac{P\, 1}{2s\, \Delta T} - \frac{\lambda_1\, 1}{2\, l_1}$$

wherein:
$\lambda$ is the thermal conduction coefficient of the material sample;
P is the amount of heat supplied by the heater in a time unit;
l is the thickness of the material sample;
s is the surface of the heater;
$\Delta T$ is the momentary temperature difference between surfaces of the material sample;
$\lambda_1$ is the thermal conduction coefficient of the reference samples; and
$l_1$ is the thickness of the reference samples.

2. The method according to claim 1, wherein the measurement of the temperature difference is carried out in a system in which all three samples are made of the same material, the value of the thermal conduction coefficient for the given momentary temperature of the system is determined from an equation:

$$\lambda_1 = \frac{P\, 1\, l_1}{s\, \Delta T(1 + 2l_1)}$$

wherein:
$\lambda_1$ is the thermal conduction coefficient of the material of which the samples are made;
P is the amount of heat supplied by the heater in a time unit;
l is the thickness of material sample;
S is the surface of the heater;
$\Delta T$ is the momentary temperature difference between surfaces of the material sample;
$l_1$ is the thickness of the reference samples.

3. The method according to claim 1 or 2, wherein said measurements are carried out at different preset rates of temperatures changes of the heat sinks.

4. The method according to claim 3, wherein the preset continuous temperature change of the two heat sinks is achieved by means of a flowing gas or liquid stream supplied by the heater, the temperature of which is continuously changed with time during said measurments.

5. The method according to claim 1, wherein the heat sinks are made of a solid body of high thermal conductivity.

* * * * *